March 9, 1937. E. J. SCHROEDER Plant Pat. 237
FREESIA
Filed April 28, 1936
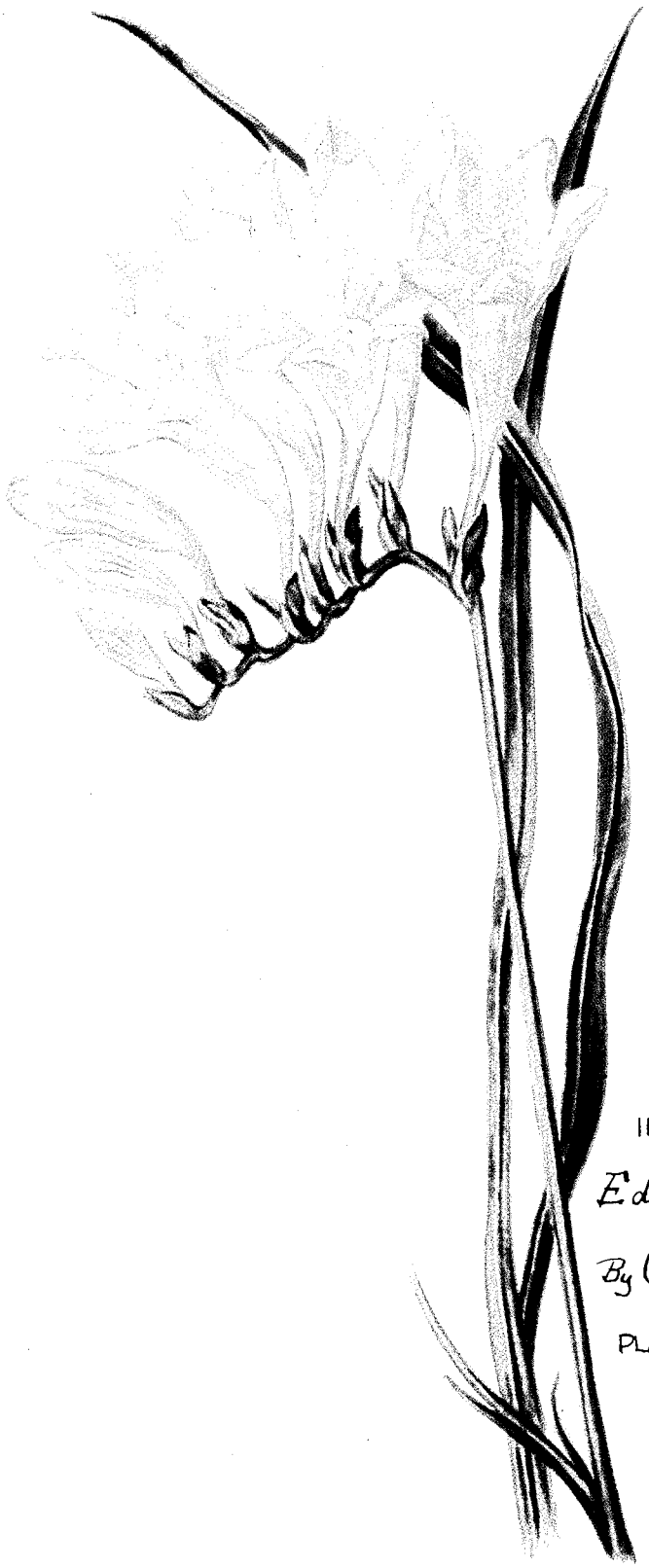
INVENTOR
Edward J. Schroeder
By Orville M Kile
PLANT PATENT AGENT Patented Mar. 9, 1937

Plant Pat. 237

UNITED STATES PATENT OFFICE

237

FREESIA

Edward J. Schroeder, Perry Hall, Md., assignor of one-half to Roman J. Irwin, New York, N. Y.

Application April 28, 1936, Serial No. 76,847

1 Claim. (Cl. 47—60)

My invention relates to improvements in fragrant white freesias. The main objects of my invention are to provide an improved freesia of a predominantly white color and excellent lasting quality, having a profusion of large-sized blossoms borne on long, strong stems.

This new freesia is a seedling of unknown origin but is probably a cross between Refracta Alba and a California seedling of white freesia which were growing in the same lot and must have been fertilized by the bees.

The accompanying illustration shows the new freesia in approximately natural size (in the original) and natural color as nearly as can be shown. Color plate references are to Ridgway's Color Standards and Nomenclature.

*The plant*

*Growth habits.*—This variety is a strong grower and an excellent producer, coming into bloom earlier than most other varieties. It grows to a height of about 30 inches. In addition to the main blossoming stem there are 3 to 5 lateral branches each bearing blossoms which open later than the main spray of blossoms.

*Stems.*—The stem or peduncle bearing the main or uppermost blossom group is ordinarily about 10 inches long to the first lateral branch. No leaf branches occur on the main stem nearer than 12 inches from the blossoms and in many cases not nearer than 18 inches. The flower stems are notably thick and strong and bear the flowers in an erect position. The usual length attained by the stems is 24 to 26 inches. The color of the stems is Oil Green (Plate V).

*Sepals or bracts.*—The two leaf-like, green sheaths at the point of attachment to the peduncle are about one-inch long and somewhat pointed.

*Leaves.*—Long and quite narrow. Rather sparse. Color of leaves Spinach Green (Plate V).

*The flowers*

*Arrangement.*—The flower groups at their prime ordinarily show four blossoms fully opened, one half-opened, one bud about to open, and one bud still in the green stage. The large number of blossoms in the group, together with the very large size of the individual blossoms, combine to make a large and showy cluster. The long strong stems hold the flowers well above the foliage, thus adding to the striking effect. The flowers are borne upright, attached to a jointed axis which is bent abruptly from the peduncle, and are set close together upon this axis.

*Shape.*—The perianth is funnel shaped, being exceptionally long and narrow at the bottom then bulging and tapering gracefully.

*Size.*—Very large. A typical flower is about 3 inches long and 1¼ to 2 inches across the top.

*Petals.*—Firm in texture. Usually six. While the usual number of segments or petals is six, each group of flowers usually includes one or sometimes two having eight fully separated and fully formed petals. The lobes are more inclined to be pointed than in other somewhat similar varieties. This effect is heightened by the tendency of the lobes to curve along the mid-line forming a valley-like effect.

*Stamens.*—Three stamens arise from the tube-like portion of the flower near its base and are attached to the throat for about an inch upward from the base of the flower. They are arranged in a group around the pistil and at one side of the open corolla. Usually the petal opposite this group of stamens bears two small spots of yellow or Light Cadmium (Plate IV).

*Anthers.*—Pure white; usually three-eighths inch long; narrow; curving sharply; stand almost vertical, being attached near one end.

*Pistil.*—Extends above anthers. Compound.

*Style.*—Pure white. Of three parts, each part having two branches.

*Ovary.*—Cylindrical. Three-celled.

*Color.*—Pure luminous white except for a Grayish Lavender (Plate XLIII) tint on some of the petals and the Light Cadmium (Plate IV) on some of the petals and in the flower throat as described below. In many specimens the lavender tint extends downward along the mid-line on the outside of the petal, often reaching half to two-thirds down toward the point of attachment. This lavender color also occurs deep inside the tube in the form of 5 or 6 streaks or lines about one-half inch long. Against the light these lines are visible from the outside.

One petal of almost every flower has on its inner surface one or two slight splotches of yellow or Light Cadmium (Plate IV) within about a half inch of its outer extremity, thus being visible when the flower is open. This same yellow or Light Cadmium (Plate IV) is prominent on the inside surface of the throat of the blossom. While the outer portion of the blossom has no yellow or Light Cadmium (Plate IV) color, the yellow from the inside imparts to the base of the funnel a greenish-yellow tinge.

*Durability.*—The keeping qualities as a cut flower are exceptionally good.

*Fragrance.*—The odor is faint but pleasantly noticeable.

*Comparisons.*—With Golden Daffodil: about the same in size of individual flowers, flowering dates, number of flowers produced in a season. With Imperial Purity: my variety is a much stronger grower, producing larger and longer stems; my variety's blooms are one-fourth larger and appear earlier.

Having thus disclosed my invention, I claim:

The variety of freesia herein shown and described, characterized particularly by its vigorous growth and profuse blooming habits resulting in the production of a large number of long and strong stems and flower spikes, the latter made up of exceptionally large flowers set close together, the flowers being mainly luminous white in appearance but marked with shades of lavender and yellow as described, and having excellent keeping qualities.

EDWARD J. SCHROEDER.